(12) United States Patent
Burov et al.

(10) Patent No.: US 8,735,623 B2
(45) Date of Patent: May 27, 2014

(54) PROCESS FOR PREPARING CREATINE AMIDES

(75) Inventors: Sergej Vladimirovich Burov, St. Petersburg (RU); Olga Sergeevna Veselkina, St. Petersburg (RU); Maria Victorovna Leko, St. Petersburg (RU)

(73) Assignee: Vertex Closed Joint Stock Company, St. Petersburg (RU)

( * ) Notice: Subject to any disclaimer, the term of this patent is extended or adjusted under 35 U.S.C. 154(b) by 45 days.

(21) Appl. No.: 13/261,286

(22) PCT Filed: Sep. 28, 2010

(86) PCT No.: PCT/RU2010/000534
§ 371 (c)(1),
(2), (4) Date: Jul. 10, 2012

(87) PCT Pub. No.: WO2011/056091
PCT Pub. Date: May 12, 2011

(65) Prior Publication Data
US 2012/0277459 A1      Nov. 1, 2012

(30) Foreign Application Priority Data
Nov. 3, 2009    (RU) .............................. 2009140380

(51) Int. Cl.
*C07C 277/08*    (2006.01)

(52) U.S. Cl.
USPC .............................................. 560/34; 560/169

(58) Field of Classification Search
CPC  C07C 227/08; C07C 279/12; C07K 5/06086; A61K 38/05
See application file for complete search history.

(56) References Cited

PUBLICATIONS

Zaragoza Dorwald, Side Reactions in Organic Synthesis, 2005, WILEY-VCH Verlag GmbH & Co. KGaA, Weinheim, Preface. p. IX.*

* cited by examiner

*Primary Examiner* — Paul A Zucker
(74) *Attorney, Agent, or Firm* — Aleksandr Smushkovich

(57) ABSTRACT

The invention relates to the field of pharmaceutical chemistry, specifically to processes for preparing biologically active substances (BAS), in particular creatine amides. What is proposed is a process for preparing creatine amides which comprises treating creatine with para-toluenesulfonic acid in an organic solvent with subsequent reaction of the resultant complex with compounds comprising a primary or secondary amino group in the presence of a condensing agent and a base which are introduced subsequently. The claimed process makes it possible to increase the yield of the end product by 2-5 times in comparison with known similar processes and also to extend the range of the compounds prepared.

5 Claims, No Drawings

PROCESS FOR PREPARING CREATINE AMIDES

CROSS-REFERENCES TO RELATED APPLICATIONS

This application is a U.S. national stage application of a PCT application PCT/RU2010/000534 filed on 28 Sep. 2010, whose disclosure is incorporated herein in its entirety by reference, which PCT application claims priority of a Russian Federation application RU2009140380 filed on 3 Nov. 2009.

FIELD OF INVENTION

The invention relates to pharmaceutical chemistry, more specifically to a methods of preparation of a new biologically active compounds, particularly to amides of creatine.

BACKGROUND OF THE INVENTION

Creatine is an endogenous nutrient occurring in a various mammalian tissues, for example, in the liver, kidneys, muscular tissue, brain tissue, blood and appears as well in the free form as in the form of creatine phosphate. Creatine is considered in a capacity of a remedy enhancing an energetic tissue metabolism, increasing an energetic reserve of ATP first of all in muscle and nerve cells.

Creatine phosphate (CrP) maintains ATP level upon increasing of energy consumption in a cell i.e. takes part in a physiological process of ADP phosphorylation with ATP formation. Among with glycogen CrP is one of main source of high-energy phosphates transformation cycle and so participates in an oxidative phosphorylation of glucose that provides an energy evolution essential for muscular tissue cells activity including skeletal muscles and cardiac muscle.

Because of creatine phosphate is able to provide ATP biosynthesis an increasing of creatine amount in muscles increases a muscular supply of creatine phosphate, enhances an energetic tissue metabolism, enhances a muscles performance capability (tolerance), increases a muscles mass.

Creatine phosphate and creatine are also an allosteric regulators of cell processes (N. Brustovetsky et al., J. Neurochem. 2001. 76. 425-434). Thus administration of 20-30 g of creatine monohydrate per day for a few days leads to increasing of total creatine content in human skeletal muscles by more than 20%. Given properties attract the special attention in view of possibility to use creatine in a capacity of nutritional supplement for organism strengthening and increasing of performance capability. Thus administration of creatine monohydrate in an amount of 15 g per day for at least 2 days is used for an increasing the muscle performance ability (WO/94/002127).

Creatine and creatine phosphate find a wide application in medicine. Thus, creatine, creatine phosphate and cyclocreatine (U.S. Pat. No. 6,706,764) are recommended for a treatment of nervous system diseases such as diabetic and toxic neuropathies, Alzheimer's disease, Parkinson's disease, stroke, etc, metabolism disturbances such as hyperglycaemia and diabetes mellitus (U.S. Pat. No. 6,193,973). Per os administration of creatine is described for a treatment of cardiac insufficiency (WO/EP 97/06225), asthma (U.S. Pat. No. 6,093,746).

Application of creatine phosphate was shown for a treatment of cardio-vascular diseases, prospectivity for a treatment of new-growth tissue (U.S. Pat. No. 5,219,846). In the mean time application of creatine and creatine phosphate are limited by bad solubility and stability in aqueous media at physiological pH values (RU 2 295 261).

Even more creatine is badly adsorbs from gastro-intestinal tract, extent of absorbtion consists a 1 to 14%. It makes necessary an administration of creatine in a high doses. For the purpose of creatine application was effective a composition manufactured at the present time is administered in amount of 20 g per day. In the mean time along with increasing of the cost of therapy administration of a high doses of creatine can lead to negative after-effects for an organism—nitrogen exchange deficit, gastro-intestinal diseases, diarrhea etc.

Therefore a preparation of creatine derivatives possessing the more stability or the more biological activity is of main interest that allows from the one hand to decrease a dose of administered compound and from another hand to find out a new field of application. Herein derivatives of creatine and variable organic acids attract the highest interest.

Thus it is known that application of creatine pyruvates (U.S. Pat. No. 6,166,249; RU 2 114 823) for an enhancement of working efficiency, body weight decreasing, adaptation to oxygen insufficiency associated with ischemia, in a capacity of nutritional supplement, for a protection of skin aging and sun light action (U.S. Pat. No. 7,186,754), for a treatment of female sexual disorders, in particular, dismenorrhea (U.S. Pat. No. 6,503,951).

Derivatives of creatine and malonic, maleic, fumaric, orotic acids and taurine (U.S. Pat. No. 6,838,562; U.S. Pat. No. 6,861,554; U.S. Pat. No. 6,166,249; U.S. Pat. No. 7,109,373) are indicated for nutritional care as a food supplement; creatine citrate (US 2004/077719) is recommended in a capacity of nootropic agent.

One of the most perspective derivatives of creatine comprises amides of creatine of general formula $NH=C(NH_2)-N(CH_3)-CH_2-CO-NH-R^*X$, wherein R is aminoacids residue or protected aminoacids residue; X-organic or mineral acid or water (RU 2 354 645) synthesized and studied by authors.

As it was determined in a process of experiments synthesized amides of creatine possessed an increased solubility and stability in aqueous solutions that allows to use it more wide in a capacity of creatine resource in an organism.

Method preparation of similar amides of creatine comprising of the most close to the claimed one upon achieved effect consist of interaction a deprotected and protected guanidilating agents with amides of sarcosine in polar organic solvents at a temperature not more than 50° C. Preparation of another derivatives of aminoacids is possible based on amides of sarcosine by using a standard chemical reactions described in literature (A. A. Gershkovich, V. K. Kibirev "Peptide Synthesis. Reagents and Methods. Kiev. "Naukova dumka". 1987).

The disadvantage of given method are multistaging, associated with requirement amides of sarcosine preliminary preparation, insufficiently high yield of desired product which in particular for Creatinyl-Glycine Benzyl Ester Hydrochloride consists of about 5%.

SUMMARY OF THE INVENTION

There is herein proposed a simple and inexpensive method for obtaining creatine amides with a higher yield thereof comprising the steps of: —conversion of creatine (Cr) to a complex soluble in organic solvents; treatment of the complex with p-toluenesulfonic acid (p-TSA) up to a complete dissolution of Cr; interaction of the complex with amino-acid derivatives including a primary or secondary amino-group, in particular, ester or amide derivatives of aliphatic or aromatic amino-acids in the presence of a condensation agent and a base consequently introduced.

PREFERRED EMBODIMENTS OF THE INVENTION

Introduction of p-TSA is carried out at least in an equimolar quantity relative to Creatine. Introduction of an amino-component and condensation agent in solution is carried out after a complete dissolution of the complex of creatine and p-TSA, and the introduction of base is carried out in 10-15 minutes after the start of the reaction and attaining a reaction equilibrium, for shifting the equilibrium in a desirable direction.

The treatment of creatine by p-TSA simultaneously results in solving a problem of conversion of creatine into solution and protection of guanidino-group by means of formation of a complex that complicates a conversion of creatine into creatinine as a result of intra-molecular cyclization.

Creatine anhydrous or cheaper Creatine hydrate were used in a capacity of Cr. Carbodiimides particularly dicyclohexylcarbodiimide, N-ethyl-N'-(3-dimethylaminopropyl)carbodiimide, diisopropylcarbodiimide or monoesters of chloroformic acid particularly ethylchloroformate, iso-butylchloroformate can be used in a capacity of condensation agent; and bases soluble in organic solvents, particularly, tertiary amines, f.e., N-morpholine, triethylamine, diisopropylamine etc. can be utilized in a capacity of base binding of hydrochloric acid evolving. Dimethylformamide, dimethylacetamide, dimethylsulfoxide, N-methylpyrrolidone etc. can be used in a capacity of organic solvents providing a completed dissolution of the complex creatine and p-TSA.

Using monoesters of chloroformic acid, particularly iso-butylchloroformate or ethylchloroformate, and dicyclohexylcarbodiimide in a capacity of condensation agent, or using diisopropylcarbodiimide in a capacity of carbodiimide are preferable as the quantity of foreign impurities is decreased, and technology of extraction of the targeted product is simplified.

A reaction mixture obtained in the process is purified generally by using ion-exchanged resins followed by recrystallization of the targeted product, which yields in 20% with a purity of more than 90%, according to the data of HPLC analysis. The basic impurity produced during the synthesis is creatinine, whose content in the targeted product generally does not exceed of 1.5%.

Amides of creatine obtained as a result of the claimed method can be further modified by using standard organic synthesis technologies.

Control of the reaction pathway and the evaluation of purity of the final and intermediate products are carried out by a method of reverse phase HPLC on a chromatograph Alliance (Waters), a column Zorbax ODS, 3.5 μm, 3×100 mm (Agilent Technologies).

A mixture of buffer solution containing 0.01 M of sodium octansulfonate and 0.02 M of sodium dihydrogen phosphate with acetonitrile is used for eluation. Detection is carried out by a method of UV-spectroscopy at a wave-length 210 nm. (Assay). The content of the basis substance in creatine amides is carried out by a method of non-aqueous titration by $HClO_4$ in presence of an indicator being crystal violet.

Determination of the molecular mass of creatine amides is carried out by a mass-spectrometry method at the time-of-flight mass-reflectrone MX-5303 with an ion source of the "Electrospray" type (Division of Institute of Energy Problem in Chemical Physics, Russian Academy of Science).

EXAMPLES OF INDUSTRIAL APPLICATIONS OF THE INVENTION

Example 1

Preparation of Creatinyl-Glycine Iso-Propyl Ester Acetate

A suspension of 5.67 g (38 mM) of creatine monohydrate in 40 mL of N,N-Dimethylformamide was placed into a 250 mL one-neck round bottom flask furnished with a dropping funnel supplied with a compensator, closed with a calcium chloride tube, then 7.23 g (38 mM) of p-Toluenesulfonic acid monohydrate was added to the suspension, while stirring with a magnetic mixer. Creatine monohydrate was completely dissolved in 5 min.

Then 6.71 g (40 mM) of Glycine iso-Propyl Ester Hydrochloride was added and the reaction mixture was cooled down to (−)10° C. at ice-salted bath after its dissolution. Then 5.24 mL (38 mM) of iso-Butylchloroformate was added, and 8.9 mL (81 mM) of N-Methylmorpholine was added via the dropping funnel during 10 minutes.

The reaction mixture was stirred at ice bath for 1 hour then a temperature was adjusted to the room condition. N-Methylmorpholine hydrochloride precipitate formed was filtered off in 10 hours, a mother liquor was evaporated at 50° C. An oily residue was dissolved in 160 mL of chloroform and kept at (−)10° C. for 10 hours.

The solution was filtered, extracted with $H_2O$ (3×100 mL). A combined aqueous phase containing the desired product was extracted with chloroform twice, an aqueous solution was evaporated in vacuum up to volume of 50 mL.

The resulted solution was flowed through a column 30×250 mm filled with a sorbent of Dowex 1×8 in the acetate form in $H_2O$. Eluent—$H_2O$, elution rate was 2 mL/min.

The column was rinsed with $H_2O$ monitoring a pH of eluate. Fractions with a pH=7 were collected, analyzed by the method of Reverse Phase HPLC, combined, an acetic acid was added and the fractions were evaporated. A residue was crystallized with 20 mL of acetonitrile at (−)10° C. for 20 hours. The resulted precipitate of Creatinyl-Glycine iso-Propyl Ester Acetate was filtered off, washed with chilled acetonitrile, diethyl ether, and dried up.

The resulted product was dissolved in 30 mL of ethanol, kept at (−)10° C. for 20 hours, the so obtained solution was filtered, ethanol was removed in vacuum, a residue was crystallized with diethyl ether. The yield of Creatinyl-Glycine iso-Propyl Ester Acetate $C_9H_{18}N_4O_3*C_2H_4O_2$ was 2.3 g (21%). Mass-spectra, found: m/z 290.29. Calculated: M 290.32. Assay of Creatinyl-Glycine iso-Propyl Ester Acetate by non-aqueous titration was 97.7% mass, creatinine impurity content was 1.5% mass.

Example 2

Preparation of Creatinyl-Glycyl-Glycine Ethyl Ester Acetate

A suspension of 4.77 g (32 mM) of Creatine monohydrate in 40 mL of N-Methylpyrrolidone was placed into a 250 mL one-neck round bottom flask furnished with a dropping funnel supplied with a compensator, closed with a calcium chloride tube, 5.02 g (35 mM) of p-Toluenesulfonic acid anhydrous was added at stirring. Creatine monohydrate was completely dissolved in 5 min.

Then 4.33 g (22 mM) of Glycyl-Glycine Ethyl Ester Hydrochloride was added and reaction mixture was cooled down to (−)10° C. at ice-salted bath after its dissolution. Then 4.51 mL (33 mM) of iso-Butylchloroformate was added and 5.1 mL (54 mM) of N-Methylmorpholine was added via the dropping funnel for 10 min. The reaction mixture was stirred at the ice bath for 1 hour, then the temperature of the mixture was adjusted to the room condition.

N-Methylmorpholine hydrochloride precipitate formed was filtered off in 10 hours mother liquor was evaporated at 50° C. The resulted oily residue was dissolved in 100 mL of chloroform and kept at (−)10° C. for 10 hours. The so obtained solution was filtered, extracted with $H_2O$ (3×100 mL).

A combined aqueous phase containing the targeted product was extracted with chloroform twice and evaporated in vacuum up to volume of 50 mL. Further purification of the targeted product was carried out according to the method described in Example 1.

Yield of $C_{10}H_{19}N_5O_4*C_2H_4O_2$ was 1.05 g (14.6%). Mass-spectra, found: m/z 273.24. Calculated: M 273.29. Assay of Creatinyl-Glycyl Glycine Ester Acetate by non-aqueous titration was 98.5% mass, creatinine impurity content was 1.3% mass.

Example 3

Preparation of Creatinyl-Glycine Methyl Ester Hydrochloride

A suspension of 2.98 g (20 mM) of Creatine monohydrate in 20 mL of Dimethylacetamide was placed into a 250 mL one-neck round bottom flask furnished with a dropping funnel supplied with a compensator, closed with a calcium chloride tube, then 3.99 g (21 mM) of p-Toluenesulfonic acid monohydrate was added at stirring on a magnetic stirrer.

A precipitate was formed and then completely dissolved in 5 min. Then 2.64 g (21 mM) of Glycine Methyl Ester Hydrochloride was added and reaction mixture was cooled down to (−)10° C. at ice-salted bath after its dissolution. Then 2.8 mL (20 mM) of iso-Butylchloroformate was added and 4.4 mL (40 mM) of N-Methylmorpholine was added via dropping funnel for 10 min.

The so obtained reaction mixture was stirred at ice bath for 1 hour then the temperature was adjusted to a room condition. N-Methylmorpholine hydrochloride precipitate formed was filtered off in 7 hours, mother liquor was evaporated at 50° C. The formed oily residue was dissolved in 80 mL of chloroform and kept at (−)10° C. for 10 hours. The resultant solution was filtered, extracted with $H_2O$ (3×100 mL).

The obtained combined aqueous phase, containing the targeted product, was extracted with chloroform (2×80 mL) and evaporated in vacuum up to a volume of 50 mL. Purification of the targeted product was carried out in an Example 1 condition with the exception of that fractions with pH=7, pH($H_2O$)=5 were collected, analyzed by the Reverse Phase HPLC, combined, hydrochloric acid was added, and the fractions were evaporated. Yield of $C_7H_{14}N_4O_3*HCl$—1.52 g (30%). Mass-spectra, found: m/z 238.65. Calculated: M 238.67. Assay of Creatinyl-Glycyl Glycine Ester Hydrochloride by non-aqueous titration—98.3% mass, creatinine impurity content—1.5% mass.

Example 4

Preparation of Creatinyl-Glycine Ethylamide Tartrate from Creatine Anhydrous

A suspension of 2.62 g (20 mM) of Creatine anhydrous in 20 mL of N,N-Dimethylformamide was placed into a 250 mL one-neck round bottom flask furnished with a dropping funnel supplied with a compensator, closed with a calcium chloride tube, then 3.83 g (20.11 mM) of p-Toluenesulfonic acid monohydrate was added at stirring on a magnetic stirrer.

The formed precipitate is completely dissolved in 10 min. Then 4.77 g (22 mM) of Glycine Ethylamide trifluoroacetate was added, and the obtained reaction mixture was cooled down to (−)10° C. at ice-salted bath after its dissolution. Then 2.8 mL (20 mM) of iso-Butylchloroformate was added, and 4.65 mL (43 mM) of N-Methylmorpholine was added via the dropping funnel during 10 minutes.

The so obtained reaction mixture was stirred at ice bath for 1 hour then the temperature was adjusted to a room condition. The precipitate formed was filtered off in 20 hours, then the mother liquor was evaporated in vacuum at 50° C. The formed oily residue was dissolved in 80 mL of chloroform and kept at (−)10° C. for 20 hours.

The so obtained solution was filtered, extracted with $H_2O$ (3×100 mL), the combined aqueous phase containing the targeted product was extracted with chloroform (2×80 mL) and evaporated in vacuum up to a volume of 50 mL. The resulted product was isolated by the method described in Example 1, with the exception of that the column with Dowex 1×8 in a tartaric form was used. Fractions with pH=7 were collected, analyzed by the Reverse Phase HPLC, combined, and evaporated. Yield of $[C_8H_{17}N_5O_2]_2*C_4H_6O_6$—3.7 g (32%). Mass-spectra, found: m/z 583.62. Calculated: M 583.61. Assay of Creatinyl-Glycine Ethylamide Tartrate by non-aqueous titration was 98.9% mass, creatinine impurity content was 0.7% mass.

Example 5

Preparation of $N^\epsilon$-Creatinyl-Lysine Ethyl Ester Diacetate

A suspension of 3.0 g (20.5 mM) of Creatine monohydrate in 40 mL of N,N-Dimethylformamide was placed into a 250 mL one-neck round bottom flask furnished with a dropping funnel supplied with a compensator, closed with a calcium chloride tube and 3.81 g (20.5 mM) of p-Toluenesulfonic acid monohydrate was added at stirring.

Then 7.0 g (20.5 mM) of a-Carbobenzoxy-L-Lysine Ethyl Ester hydrochloride was added and the formed reaction mixture was cooled down to (−)10° C. at ice-salted bath after its dissolution. Then 2.8 mL (20.5 mM) of iso-Butylchloroformate was added, and 4.4 mL (20.5 mM) of N-Methylmorpholine was added via the dropping funnel during 10 minutes.

The so formed reaction mixture was stirred at ice bath for 1 hour, then the temperature was adjusted to a room condition. The resulted suspension was filtered, mother liquor was evaporated in vacuum at 50° C.

The resulted oily residue was dissolved in 150 mL of n-butanol, washed with $NaHCO_3$ 5% four times, then with $H_2O$ twice. Thereafter, n-butanol was evaporated, 30 mL of $H_2O$ was added to the residue and the resulted suspension was applied onto the column with sorbent YMC*Gel ODS 22.5× 150 equilibrated with 0.2% aqueous solution of acetic acid; the column was eluted with 0.2% aqueous solution of acetic acid then eluted in a gradient rate up to 10% of iso-propyl alcohol in 0.2% aqueous solution of acetic acid.

The resulted fractions were analyzed by qualitative reaction and HPLC, combined, and evaporated. The obtained residue was crystallized with 5 mL of acetonitrile, filtered off, and dried up in vacuum. Yield of $C_{20}H_{31}N_5O_5*C_2H_4O_2$ was $N^\alpha$-Carbobenzoxy-$N^\epsilon$-Creatinyl-Lysine Ethyl Ester Acetate 1.5 g (18%). Mass-spectra, found: m/z 481.77. Calculated: M 481.77. Assay of $N^\alpha$-Carbobenzoxy-$N^\epsilon$-Creatinyl-Lysine Ethyl Ester Acetate by non-aqueous titration was 98.9% mass, creatinine impurity content was 1.0% mass.

1.0 g of $N^\alpha$-Carbobenzoxy-$N^\epsilon$-Creatinyl-Lysine Ethyl Ester Acetate prepared was dissolved in 10 mL of methanol and hydrogenated over Pd black for 3 hours. The completeness of carbobenzoxy-group leaving was controlled by TLC in the system acetonitrile-$H_2O$-acetic acid (6:1:1).

Catalyst was filtered off, 1.0 mL of acetic acid was added to a mother liquor and evaporated. The so obtained product was filtered off, washed with chilled acetonitrile, diethyl ether, and dried up in vacuum. Yield of $C_{12}H_{25}N_5O_3*2C_2H_4O_2$-$N^\epsilon$-Creatinyl-Lysine Ethyl Ester diacetate 0.2 g (42%). Mass-spectra, found: m/z 407.34. Calculated: M 407.46. Assay of $N^E$-Creatinyl-Lysine Ethyl Ester diacetate by non-aqueous titration was 99.2% mass, creatinine impurity content was 0.5% mass.

Example 6

Preparation of Creatinyl-Phenylalanine Ethylamide Hydrochloride from Creatine Anhydrous A suspension of 2.62 g (20 mM) of Creatine monohydrate in 20 mL of Dimethylsulfoxide was placed into a 250 mL one-neck round bottom flask furnished with a dropping funnel supplied with a compensator, closed with a calcium chloride tube and 3.83 g (20.11 mM) of p-Toluenesulfonic acid monohydrate was added at stirring on a magnetic stirrer. The precipitate was completely dissolved in 10 min.

Then 6.71 g (20 mM) of Phenylalanine ethylamide trifluoroacetate was added reaction mixture was cooled down to (−)10° C. at ice-salted bath after its dissolution. Then 2.8 mL (20 mM) of iso-Butylchloroformate was added and 4.65 mL (43 mL) of morpholine. The reaction mixture was stirred at ice bath for 1 hour then the temperature was adjusted to a room condition.

The precipitate formed was filtered off, and then the mother liquor was evaporated at 50° C. An oily residue was dissolved in 80 mL of chloroform and kept at (−)10° C. for 20 hours. The obtained solution was filtered and extracted with $H_2O$ (3×100 mL), a combined aqueous phase containing the targeted product was extracted with chloroform (2×80 mL) and evaporated in vacuum up to a volume of 50 mL. Further purification of the targeted product was carried out according to the method described in Example 1.

The resulted product was isolated by the method used in Example 1, with the exception of that the fractions with pH=7 were collected, analyzed by Reverse Phase HPLC, combined, added with a 1M solution of hydrochloric acid, and thereafter the fractions were evaporated. Yield of $C_{15}H_{23}N_5O_2*HCl$ was Creatinyl-Phenylalanine Ethylamide Hydrochloride 3.7 g (32%). Mass-spectra, found was m/z 341.87. Calculated: M 341.84. Assay of Creatinyl-Phenylalanine Ethylamide Hydrochloride by non-aqueous titration was 99.3% mass, creatinine impurity content was 0.5% mass.

Example 7

Preparation of Creatinyl-Glycyl-Alanine Ethyl Ester Hemisuccinate

A suspension of 2.0 g (13.4 mM) of Creatine monohydrate in 10 mL of Dimethylformamide was placed into a 100 mL one-neck round bottom flask furnished with a dropping funnel supplied with a compensator, closed with a calcium chloride tube and 2.54 g (13.4 mM) of p-Toluenesulfonic acid monohydrate was added at stirring on a magnetic stirrer and then 1.41 g (6.7 mM) of Glycyl-Alanine Ethyl Ester Hydrochloride, 1.38 g (6.7 mM) of dicyclohexylcarbodiimide in 2 mL of Dimethylformamide. Then 1.14 mL (6.7 mM) of diisopropylethylamide was added via the dropping funnel in 10 min.

The so obtained reaction mixture was kept for 20 hours at a room temperature, a solid of dicyclohexylcarbodiimide hydrochloride and dicyclohexylurea hydrochloride was filtered off, the mother liquor was evaporated at 50° C. An oily residue was dissolved in 100 mL of chloroform and extracted with $H_2O$ (3×100 mL). A combined aqueous phase containing the targeted product was extracted with chloroform twice and evaporated in vacuum up to a volume of 20 mL. The resulted solution was eluted with $H_2O$ through a column 30×150 mm with Dowex 2×8 in a succinic form. The elution rate was 2 mL/min.

The column was eluted with $H_2O$ monitoring a pH value of the eluent. Fraction with pH 6÷7 were collected, combined and evaporated. A residue was crystallized with 10 mL of acetonitrile at (−)10° C. for 5 hours. A solid of Creatinyl-Glycyl-Alanine Ethyl Ester Hemisuccinate was filtered off, washed with chilled acetonitrile, diethyl ether and dried. A yield of crude product was 1.8 g.

The so obtained product was dissolved in 10 mL of ethanol, kept at (−)10° C. for 10 hours, the resulted solution was filtered. The rested mother liquor was evaporated, a residue was dissolved in 5 mL of $H_2O$ and applied onto the column with sorbent YMC*Gel ODS 22.5×150 equilibrated with 0.05% aqueous solution of succinic acid.

The column was eluted with 0.2% succinic acid, fractions were monitored by HPLC. Fractions containing a desired product with a purity not less than 95% were evaporated. The residue was dried by distillation with iso-propanol and crystallized with diethyl ether. Yield of $C_{11}H_{21}N_5O_4*0.5C_4H_6O_4$—Creatinyl-Glycyl-Alanine Ethyl Ester Hemisuccinate was 0.56 g (24%). Mass-spectra, found: m/z 346.33. Calculated: M 346.36. Assay of Creatinyl-Glycyl-Alanine Ethyl Ester Hemisuccinate by non-aqueous titration was 99.4% mass, creatinine impurity content by HPLC was 0.8% mass.

Example 8

Preparation of Creatinyl-γ-Aminobutyric Acid Ethyl Ester Acetate

A suspension of 4.20 g (32 mM) of Creatine in 40 mL of Dimethylformamide was placed into a 250 mL one-neck round bottom flask furnished with a dropping funnel supplied with a compensator, closed with a calcium chloride tube and 5.02 g (35 mM) of p-Toluenesulfonic acid monohydrate was added at stirring, 5.36 g (32 mM) of γ-aminobutyric acid ethyl ester hydrochloride, and the reaction mixture was cooled down to (−)10° C. at ice-salted bath after its dissolution.

Then 3.2 mL (33 mM) of ethylchloroformate was added, 5.1 mL (54 mM) of N-Methylmorpholine was added via the dropping funnel during 10 minutes. The reaction mixture was stirred at ice bath for 1 hour then the temperature was adjusted to a room condition.

In 10 hours, the residue of N-Methylmorpholine hydrochloride formed was filtered off, the mother liquor was evaporated at 50° C. The residue was recrystallized with iso-propanol, purified by ion-exchanged chromatography on a column with Sephadex SE-C25 in pyridine-acetate buffer solution. Fractions containing of the targeted product were combined, evaporated. Yield of $C_{10}H_{20}N_4O_3*C_2H_4O_2$ was Creatinyl-γ-aminobutyric acid ethyl ester acetate was 1.95 g (25.0%). Mass-spectra, found was m/z 304.34. Calculated: M 304.35. Assay of Creatinyl-γ-aminobutyric acid ethyl ester acetate by non-aqueous titration was 98.7% mass, creatinine impurity content by HPLC was 1.2% mass.

Example 9

Preparation of Creatinyl-Alanine Ethyl Ester Acetate

A suspension of 2.0 g (13.4 mM) of Creatine monohydrate in 10 mL of Dimethylformamide was placed into a 100 mL one-neck round bottom flask furnished with a dropping funnel supplied with a compensator, closed with a calcium chloride tube and 2.54 g (13.4 mM) of p-Toluenesulfonic acid was added at a stirring on a magnetic stirrer and then 1.01 g (6.7 mM) of Alanine Ethyl Ester hydrochloride, 0.85 g (6.7 mM) of diisopropylcarbodiimide in 2 mL of Dimethylformamide. Then 0.94 mL (6.7 mM) of triethylamine was added via the dropping funnel during 10 minutes.

The reaction mixture was kept for 20 hours at a room temperature, a precipitate of diisopropylethylamine and diisopropylurea hydrochlorides was filtered off, a mother liquor was evaporated at 50° C. An oily residue was dissolved in 100 mL of chloroform and extracted with $H_2O$ (3×100 mL). A combined aqueous phase containing the targeted product was extracted with chloroform twice and evaporated at a rotor evaporator to a volume of 20 mL.

The resulted solution was eluted with $H_2O$ through a column 30×150 mm with Dowex 2×8 in acetate form. Elution rate was 2 mL/min. The column was eluted with $H_2O$ monitoring a pH of the eluate. Fractions with pH 6÷7 were collected, combined, evaporated. The remaining mixture was crystallized with 10 mL of acetonitrile at (−)10° C. for 5 hours.

A residue of Creatinyl-Alanine Ethyl Ester acetate was filtered off, washed with chilled acetonitrile, diethyl ether and dried up. Yield of $C_9H_{18}N_4O_3*C_2H_4O_4$—Creatinyl-Alanine Ethyl Ester acetate was 0.56 g (24%). Mass-spectra, found was m/z 290.35. Calculated: M 290.31. Assay of Creatinyl-glycylalanine ethyl ester acetate by non-aqueous titration was 99.1%, creatinine impurity content by HPLC was 0.9% mass.

Example 10

Preparation of Creatinyl-Phenylalanine Ethyl Ester Acetate

A suspension of 11.3 g (86 mM) of Creatine in 80 mL of Dimethylformamide was placed into a 250 mL one-neck round bottom flask furnished with a dropping funnel supplied with a compensator, closed with a calcium chloride tube and 16 g (86 mM) of p-Toluenesulfonic acid monohydrate was added at stirring on a magnetic stirrer. A precipitate was completely dissolved in 5 minutes.

Then 11.5 g (50 mM) of Phenylalanine Ethyl Ester hydrochloride and 7.75 mL (45 mM) of diisopropylcarbodiimide were added. Then 8.6 mL (50 mM) of diisopropylethylamine was added via the dropping funnel for 10 min. The reaction mixture was kept for 20 hours at a room temperature, then 10 mL of $H_2O$ was added, a precipitate of diisopropylurea formed was filtered off, a resulted solution was analyzed by HPLC. According analysis, the reaction was completed at 50%.

A resulted product was isolated by the method described in Example 1 with an exception of that the fractions with pH=7, pH($H_2O$)=5 were collected, analyzed by Reversed Phase HPLC, combined, added with 1M solution of acetic acid and evaporated. Yield of $C_{15}H_{22}N_4O_3*C_2H_4O$—Creatinyl-Phenylalanine Ethyl Ester Acetate was 7.9 g (25%). Mass-spectra, found was m/z 366.37. Calculated: M 366.41. Assay of Creatinyl-Phenylalanine Ethyl Ester acetate by non-aqueous titration was 99.4%, creatinine impurity content by HPLC was 0.7% mass.

Study of Amides of Creatine Neuroprotective Activity

Research described here and herein below was carried out by using the following amides of creatine prepared according to the claimed method:
1. Creatinyl-Glycine iso-Propyl Ester Acetate
2. Creatinyl-Glycyl-Glycine Ethyl Ester Acetate
3. Creatinyl-Glycine Ethylamide Tartrate
4. $N^\epsilon$-Creatinyl-Lysine Ethyl Ester Diacetate
5. Creatinyl-Phenylalanine Ethylamide Hydrochloride
6. Creatinyl-γ-Aminobutyric acid Ethyl Ester acetate.

Research of the neuroprotective action of amides of creatine was carried out in a rat model of focal ischemia (male, Wistar, 12÷14 weeks, 220÷240 g). Anesthesia was performed by sodium thiopental 60 mg/kg. A solution of amides of creatine in saline was administered intravenous to the first group of animals 45 min before ischemia, saline was administered to a control group, a solution of amides of creatine in saline was administered intragastric per os by an enteral tube a day before ischemia to the second group of animals 3 times per day, saline was administered to a control group.

Endovascular occlusion of middle cerebral artery was carried out by the method of Koizumi J. et al (1986) in the modification of Longa E. Z. et al (1989) and Belayev L. et al (1999). Standard time of ischemia constituted 30 min, standard time of reperfusion constituted 48 hour. The animals were sacrificed, brain slices with thickness of 2 mm were produced for assessing a brain damage volume. The damage area was determined by staining with phenyltetrazolium chloride followed by data acquisition and analysis of stained slice digital images. A brain damage coefficient, i.e. a relation of damage area to the slice surface was calculated (Table 1).

TABLE 1

Effect of amides of creatine on a brain damage in male rat Wistar associated with experimental ischemia/reperfusion ($p < 0.05$).

| Agent | Method of administration, dose (n = 5) | Brain damage coefficient, % |
|---|---|---|
| Agent 1 | i./v.; 150 mg/kg | 11.2 ± 2.3 |
| Agent 2 | i./v.; 200 mg/kg | 12.1 ± 2.0 |
| Agent 3 | i./v.; 150 mg/kg | 12.0 ± 1.7 |
| Agent 4 | i./v.; 100 mg/kg | 13.3 ± 3.2 |
| Agent 5 | i./v.; 50 mg/kg | 14.0 ± 1.1 |
| Agent 6 | i./v.; 45 mg/kg | 13.1 ± 1.0 |
| Saline | i./v. | 19.4 ± 5.3 |
| Agent 1 | per os; 3 × 150 mg/kg | 14.2 ± 3.0 |
| Agent 3 | per os; 3 × 150 mg/kg | 13.9 ± 3.3 |
| Agent 4 | per os; 3 × 100 mg/kg | 15.2 ± 2.9 |
| Saline | per os | 21.4 ± 4.7 |

Study of Amides of Creatine Effect on a Retention of Cognitive Function Associated with Cerebral Ischemia Cerebral ischemia was induced by the method mentioned above. A solution of amides of creatine or saline was administered intravenous. The score scale of Garcia et al (1955) was used for assessing neurological deficit associated with focal ischemic and reperfusion cerebral damage. Testing the animals was carried out before ischemia, on a second and third days after ischemia-reperfusion at a fixed time for exclusion of behavioral changes by means of circadian rhythm. Spontaneous activity, symmetrical limb movement, climbing onto vertical reticulated wall, body proprioreception, touching to vibriss were assessed. A maximum point by assigned score was 18 (lack of neurological deficit), minimum—3 (severe neurological deficit). The results were listed in Table 2.

TABLE 2

Neurological condition in rat by Garcia score on $2^{nd}$ and $3^{rd}$ days after ischemia (p < 0.05).

| Agent, dose | Neurological condition by Garcia score | | |
|---|---|---|---|
| | 1 day before ischemia | $2^{nd}$ day after ischemia | $3^{rd}$ day after ischemia |
| Agent 1; 150 mg/kg | 18 ± 0 | 10 ± 2 | 15 ± 2 |
| Agent 3; 150 mg/kg | 18 ± 0 | 11 ± 2 | 16 ± 1 |
| Agent 4; 100 mg/kg | 18 ± 0 | 14 ± 1 | 17 ± 2 |
| Agent 5; 50 mg/kg | 18 ± 0 | 11 ± 1 | 14 ± 1 |
| Agent 6; 45 mg/kg | 18 ± 0 | 14 ± 0 | 16.0 ± 1.1 |
| Saline | 18 ± 0 | 6 ± 1 | 9 ± 2 |

Study of Amides of Creatine Stability in Artificial Gastric Secretion and Human Plasma.

10 mg of amides of creatine was dissolved in 20 mL of artificial gastric secretion for study of amides of creatine stability, solution aliquot was place into vial for chromatograph. Vial with solution was place into chromatograph autosampler at 37° C. Initial concentration of amides of creatine and its relative change in gastric secretion were determined by HPLC at indicated temperature (Table 3).

TABLE 3

Stability of creatine analoques in gastric secretion at a temperatute of 37° C.

| Agent | Stability, % | | | |
|---|---|---|---|---|
| | 0 hour | 1 hour | 3 hours | 5 hours |
| Agent 1 | 100 | 100 | 99 | 97 |
| Agent 2 | 100 | 100 | 98 | 98 |
| Agent 3 | 100 | 100 | 97 | 98 |
| Agent 4 | 100 | 100 | 98 | 97 |
| Agent 5 | 100 | 100 | 98 | 99 |
| Agent 6 | 100 | 100 | 99 | 99 |

Stability of amides of creatine in human plasma was assessed by relative change in concentration of amides of creatine in plasma. 1 mL of plasma was mixed with 0.2 mL of amides of creatine aqueous solution with concentration 5 mg/mL, a mixture was kept at a temperature of 37° C., aliquot of volume 0.2 mL was drawn in fixed time ranges, mixed with 0.02 mL of trifluoroacetic acid 10% solution, a precipitate was centrifuged at 3 00 g for 20 min. A concentration of amides of creatine in supernatant was determined by HPLC method (Table 4).

TABLE 4

Stability of creatine analoques in human plasma at a temperature of 37° C.

| Agent | Stability, % | | | |
|---|---|---|---|---|
| | 0 hour | 0.25 hour | 0.5 hours | 1 hour |
| Agent 1 | 100 | 100 | 99 | 91 |
| Agent 2 | 100 | 100 | 97 | 90 |
| Agent 3 | 100 | 100 | 95 | 90 |
| Agent 4 | 100 | 100 | 100 | 89 |
| Agent 5 | 100 | 100 | 97 | 87 |

The results presented herein above show that amides of creatine can be prepared by using the claimed method representing a simpler technology, from heaper raw material and with a higher yield. The prepared amides of creatine are of interest for applications in medicine as they possess a neuroprotective action.

The invention claimed is:

1. A method for preparation of amides of creatine, comprising the steps of:
   treatment of Creatine by p-Toluenesulfonic acid in an organic solvent thereby obtaining a complex; wherein said organic solvent is one of the following:
   Dimethylacetamide, or N-Methylpyrrolidone, or Dimethylsulfoxide, or N,N-Dimethylformamide;
   interaction of said complex with amino acid derivatives containing a primary or a secondary amino group in the presence of a condensation agent and a consequently introduced base soluble in organic solvents in a quantity providing the binding of evolved acid,
   wherein said condensation agent is represented by one of the following:
   dicyclohexylcarbodiimide,
   diisopropylcarbodiimide,
   iso-Butylchloroformate, and
   Ethylchloroformate;
   wherein said base is one of the following:
   N-methylmorpholine,
   triethylamine, and
   diisopropylethylamine.

2. The method according to claim 1, wherein said treatment is carried out at least in an equimolar quantity relative to Creatine.

3. The method according to claim 1, wherein Creatine is anhydrous Creatine.

4. The method of claim 1, wherein Creatine is Creatine monohydrate.

5. The method of claim 1, wherein said amino acid derivatives are ester or amide derivatives of aliphatic or aromatic amino acids.

* * * * *